United States Patent
Chen et al.

(10) Patent No.: US 11,759,445 B2
(45) Date of Patent: Sep. 19, 2023

(54) USE OF RIVASTIGMINE IN PREPARATION OF ANTI-RADIATION MEDICAMENT

(71) Applicant: Soochow University, Jiangsu (CN)

(72) Inventors: Qiu Chen, Jiangsu (CN); Fengmei Cui, Jiangsu (CN); Hongbin Yan, Jiangsu (CN)

(73) Assignee: SOOCHOW UNIVERSITY, Suzhou (CN)

( * ) Notice: Subject to any disclaimer, the term of this patent is extended or adjusted under 35 U.S.C. 154(b) by 46 days.

(21) Appl. No.: 17/444,041

(22) Filed: Jul. 29, 2021

(65) Prior Publication Data
US 2022/0175714 A1    Jun. 9, 2022

(30) Foreign Application Priority Data
Dec. 8, 2020    (CN) .......................... 202011461450.2

(51) Int. Cl.
*A61K 31/27*    (2006.01)
*A61P 39/00*    (2006.01)

(52) U.S. Cl.
CPC .............. *A61K 31/27* (2013.01); *A61P 39/00* (2018.01)

(58) Field of Classification Search
None
See application file for complete search history.

(56) References Cited

U.S. PATENT DOCUMENTS

| | | | | |
|---|---|---|---|---|
| 6,565,883 B2 * | 5/2003 | Ogorka | ................ | A61K 9/5078 424/490 |
| 2009/0004281 A1 * | 1/2009 | Nghiem | ................ | A61K 31/554 424/490 |
| 2018/0125785 A1 * | 5/2018 | Park | ....................... | A61K 47/38 |

FOREIGN PATENT DOCUMENTS

| WO | WO-2007002356 A2 * | 1/2007 | ............. A23L 33/15 |
|---|---|---|---|
| WO | WO-2014071389 A1 * | 5/2014 | ............. A61K 31/22 |

OTHER PUBLICATIONS

Oto, Berna, et al. "The interaction of gamma radiation with drugs used in cholinergic medications." International Journal of Radiation Biology 96.2 (Feb. 2020): 236-244. (Year: 2020).*
Ellis, Frank. "Radiation Sickness." Acta Radiologica 41:sup116 (1954): 365-375. DOI: 10.3109/00016925409177209 (Year: 1954).*
Özyurt, Hazan, et al. "Investigation into the role of the cholinergic system in radiation-induced damage in the rat liver and ileum." Journal of radiation research 55.5 (2014): 866-875. (Year: 2014).*
Isikli, Zekiye, and Berna Oto. "Gamma or X-rays attenuation properties of some biochemical compounds." Radiation Effects and Defects in Solids 172.3-4 (2017): 296-304. (Year: 2017).*
Smith, Tyler A., et al. "Radioprotective agents to prevent cellular damage due to ionizing radiation." Journal of translational medicine 15 (2017): 1-18. (Year: 2017).*

* cited by examiner

*Primary Examiner* — Bethany P Barham
*Assistant Examiner* — Peter Anthopolos
(74) *Attorney, Agent, or Firm* — SALIWANCHIK, LLOYD & EISENSCHENK

(57) ABSTRACT

The present disclosure relates to use of Rivastigmine in the preparation of an anti-radiation medicament, and belongs to the field of medical technology. The present disclosure provides use of Rivastigmine in the preparation of an anti-radiation medicament. Researches show that Rivastigmine significantly promoted the proliferation of Lgr5$^+$ stem cells receiving 10 Gy radiation (after being irradiated with 10 Gy radiation for 10 d, Lgr5$^+$ stem cells cultured in a Rivastigmine-containing culture solution had an increment 14.2 times of that of the Lgr5$^+$ stem cells cultured in a Rivastigmine-free culture solution). Rivastigmine also significantly reduced the mortality of mice after being irradiated with 10 Gy radiation (after receiving 10 Gy whole body irradiation, all the mice not intraperitoneally injected Rivastigmine died within 10 d; and for the mice intraperitoneally injected Rivastigmine, the survival rate of the mice was still greater than 40% 30 d later), and thus might have good radiation-proof effect.

9 Claims, 6 Drawing Sheets

USE OF RIVASTIGMINE IN PREPARATION OF ANTI-RADIATION MEDICAMENT

CROSS REFERENCE TO RELATED APPLICATION

This patent application claims the benefit and priority of Chinese Patent Application No. 202011461450.2, filed on Dec. 8, 2020, the disclosure of which is incorporated by reference herein in its entirety as part of the present application.

TECHNICAL FIELD

The present disclosure relates to use of Rivastigmine in the preparation of an anti-radiation medicament, and belongs to the field of chemical technology.

BACKGROUND ART

The widespread use of ionizing radiation brings lots of benefits as well as numerous risks to the human being. It is more obvious when the ionizing radiation is used in nuclear energy. For example, the Chernobyl nuclear accident in 1986, the Fukushima nuclear accident in 2011, and the like have brought us server disasters.

People may suffer radiation sickness after receiving a certain dose of ionizing radiation and have acute gastrointestinal syndrome after receiving 10-50 Gy ionizing radiation in a short time. One can also have nausea, emesis and diarrhea rapidly caused by the death of intestinal mucosa stem cells, followed by repeated gastrointestinal symptoms, blood poisoning, and electrolyte imbalance after about one week of incubation, resulting in the possibility of death. The radiation protection of intestinal injury is always the research hotspot and difficulty in the field of radiation biology.

Rivastigmine is a kind of medicament for treating Alzheimer's disease, and can enhance neurons to release cholinergic substances in brain by inhibiting acetylcholin esterase, thus improving the cognition of Alzheimer's disease patients.

Currently, there is no report on the use of Rivastigmine in the preparation of an anti-radiation medicament.

SUMMARY

The present disclosure is intended to provide a novel use of Rivastigmine; that is, to provide use of Rivastigmine in the preparation of an anti-radiation medicament.

To solve the above problem, the present disclosure further provides use of Rivastigmine in the preparation of a medicament, wherein the medicament has at least one of the following applications:

(a) anti-radiation; and/or,
(b) promotion in the proliferation of $Lgr5^+$ stem cells.

In an embodiment of the present disclosure, the radiation is ionizing radiation.

In an embodiment of the present disclosure, the ionizing radiation may include radiation from a ray and a radioactive substance.

In an embodiment of the present disclosure, the ray may be selected from an X-ray, $\alpha$-ray, $\beta$-ray, $\gamma$-ray, neutron ray, negative $\pi$-meson ray and heavy ion beam.

In an embodiment of the present disclosure, the heavy ion beams may be selected from a helium ion beam, carbon ion beam, nitrogen ion beam, oxygen ion beam and neon ion beam.

In an embodiment of the present disclosure, the medicament may contain Rivastigmine, a medicament carrier and/or a pharmaceutical adjuvant.

In an embodiment of the present disclosure, the medicament carrier may contain microcapsules, microspheres, nanoparticles and/or lipidosome.

In an embodiment of the present disclosure, the pharmaceutical adjuvant may be selected from a solvent, a propellant, a solubilizer, a cosolvent, an emulsifier, a colorant, a binding agent, a disintegrant, a filler, a lubricant, a wetting agent, an osmotic pressure regulator, a stabilizer, a flow aid, a corrigent, a preservative, a suspending agent, a coating material, an aromatic, an anti-binding agent, a chelating agent, a penetration enhancer, a pH regulator, a buffering agent, a plasticizer, a surfactant, a foaming agent, an anti-foaming agent, a thickener, a clathrate compound, a humectant, an absorbent, a diluent, a flocculant, a deflocculant, a filter aid, and/or a release retardant.

In an embodiment of the present disclosure, the medicament may have a dosage form that is selected from a powder, a tablet, a granule, a capsule, a solution, an emulsion, a suspension and an injection.

The technical solution of the present disclosure has the following advantages:

The present disclosure provides use of Rivastigmine in the preparation of an anti-radiation medicament. Researches show that Rivastigmine significantly promoted the proliferation of $Lgr5^+$ stem cells receiving 10 Gy radiation (after being irradiated with 10 Gy radiation for 10 d, $Lgr5^+$ stem cells cultured in a Rivastigmine-containing culture solution had an increment 14.2 times of that of the $Lgr5^+$ stem cells cultured in a Rivastigmine-free culture solution). Rivastigmine also significantly reduced the mortality of mice after being irradiated with 10 Gy radiation (after receiving whole body irradiation with 10 Gy radiation, all the mice without intraperitoneally injecting Rivastigmine died within 10 d; and for the mice intraperitoneally injected with Rivastigmine after receiving 10 Gy whole body irradiation, the survival rate of the mice was still greater than 40% 30 days post irradiation), thus may have good radiation-proof effect.

DETAILED DESCRIPTION OF THE EMBODIMENTS

Figure 1:
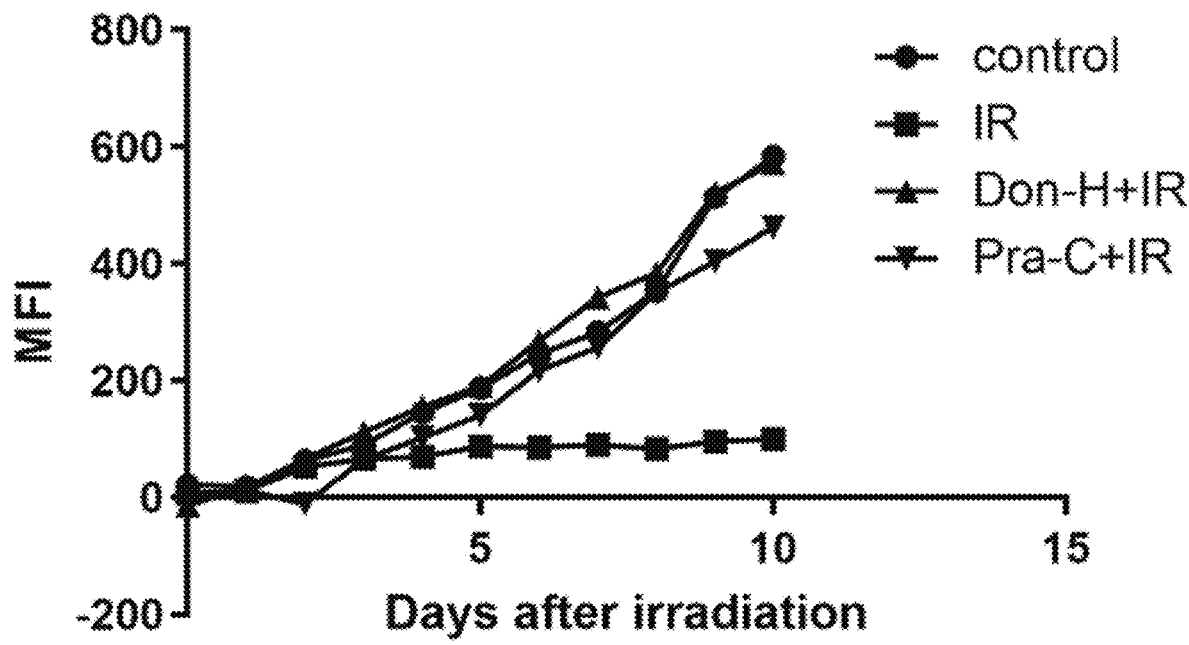
FIGS. 1-4 show mean fluorescence intensity (MFI) of crypt stem cells $Lgr5^+$ of mice in different groups.

The following examples serve to provide further appreciation of the present disclosure, but are not limited to the preferred examples and do not limit the spirit and scope of the disclosure; any product that is the same as or similar to the disclosure made in light of the disclosure or by combination of the present disclosure with other features of the prior art shall fall within the scope of the disclosure.

If specific experimental procedure or conditions are not indicated in the present disclosure, operations or conditions of conventional experimental procedures known in the art shall be used. If manufacturers of reagents and apparatus used are not indicated, conventional reagent products may be commercially available.

Example 1: Influences of Different Medicaments on Irradiated Cells or Mice

1.1 Experimental Materials

1.1.1 Experimental Animal 4 to 6 week-old C57BL/6 male mice (SPF level) were purchased from Model Animal Research Center of Nanjing University. Lgr5-EGFP-ires-CreERT2 (Lgr5-GFP) mice were purchased from The Jackson Laboratory (USA). All mice were raised in an SPF laboratory animal room of Soochow University Animal Management Center. All drinking water, conventional feeds, paddings and various experimental supplies entering to the animal room were sterilized by high temperature, high pressure or irradiation, subjected to strict microorganism control, and shall strictly observe the rules and regulations of the SPF laboratory animal room.

1.1.2 Main Reagents and Consumables

1) Bioactive Compound Library (790 types: Plinabulin (NPI-2358), Imiquimod, Flavopiridol (Alvocidib), Tamoxifen, CHIR-99021 (CT99021), Celastrol, Ellagic acid, Gatifloxacin, Bafetinib (INNO-406), Tenofovir, Prazosin HCl, Tamsulosin hydrochloride, Ofloxacin, Marbofloxacin, Fludarabine, Irbesartan, Norfloxacin, Lactulose, Sulfapyridine, Theophylline, Alendronate sodium trihydrate, Methyldopa, Betamethasone Dipropionate, Betamethasone Valerate, Torsemide, Eplerenone, Fomepizole, Paliperidone, NEXIUM (esomeprazole magnesium), Oxybutynin, Tetrabenazine (Xenazine), Amlodipine Besylate, Betaxolol HCl, Flubendazole, Sarafloxacin HCl, Meclizine 2HCl, Pramipexole 2HCl Monohydrate, ENMD-2076 L-(+)-Tartaric acid, Oxytetracycline Dihydrate, Cyclophosphamide Monohydrate, Rosiglitazone HCl, Dexmedetomidine HCl, Vinpocetine, Lapatinib, Neratinib (HKI-272), Sitafloxacin Hydrate, Taladegib (LY2940680), Bazedoxifene Acetate, A-966492, R788 (Fostamatinib) Disodium, PF-3716556, Neohesperidin Dihydrochalcone (Nhdc), L-carnitine, (S)-10-Hydroxycamptothecin, Gambogic Acid, Rosiglitazone maleate, Sulfadoxine, Amiloride HCl dihydrate, Prednisolone Acetate, Trazodone HCl, Oseltamivir Phosphate, PF-2545920, Nepicastat (SYN-117) HCl, GSK1070916, CHIR-98014, Tivantinib (ARQ 197), AT406 (SM-406), TH-302, Tideglusib, GW441756, MLN0905, TDZD-8, Fenoprofen calcium hydrate, Enrofloxacin, Tazobactam, Dexamethasone Acetate, Erythromycin Ethylsuccinate, Levobupivacaine HCl, Clopidol, Azithromycin Dihydrate, Chlortetracycline HCl, Tenatoprazole, Amoxapine, Deoxycorticosterone acetate, Ebastine, Micafungin Sodium, Salmeterol Xinafoate, (R)-(+)-Atenolol HCl, 9-Aminoacridine, Anisotropine Methylbromide, Benzthiazide, Carbadox, Diphenylpyraline HCl, Disopyramide Phosphate, Ethoxzolamide, Isoetharine Mesylate, Mepiroxol, Mesoridazine Besylate, Metaproterenol Sulfate, Metaraminol Bitartrate, Meticrane, Moxalactam Disodium, Nalmefene HCl, Nialamide, Oxethazaine, Pentoxifylline, Piromidic Acid, Procyclidine HCl, Ractopamine HCl, Terfenadine, Tolazamide, Tacrine HCl, Pimozide, Carbachol, Glafenine HCl, Phthalylsulfacetamide, Carbenoxolone Sodium, Nicotine Ditartrate, Dicyclomine HCl, Thioridazine HCl, Mepenzolate Bromide, Aceclidine HCl, Imipramine HCl, Proadifen HCl, Pyrilamine Maleate, Difloxacin HCl, Fosfomycin Tromethamine, Bephenium Hydroxynaphthoate, Brucine sulfate salt hydrate, Camylofin Chlorhydrate, Clofoctol, Diperodon HCl, Isoxicam, Nifenazone, Oxeladin Citrate, Pasiniazid, Procodazole, Sodium 4-aminohippurate Hydrate, Trimipramine Maleate, Nitenpyram, Naloxone HCl Dihydrate, Eltrombopag, Calcium D-Panthotenate, 6-Mercaptopurine (6-MP) Monohydrate, Vinblastine sulfate, Acetazolamide, 17-Hydroxyprogesterone, 2,2,2-Tribromoethanol, 4-Aminoantipyrine, 4-Aminobenzoic acid, 6-Benzylaminopurine, Aceglutamide, Acetylleucine, Ademetionine disulfate tosylate, (+)-Camphor, Cefotaxime sodium, Chloroxylenol, Citric acid trilithium salt tetrahydrate, DEET, Dehydroacetic acid, Ethylparaben, Fenbufen, Fenofibric acid, Furazolidone, Idramantone, i-Inositol, Iopamidol, Methylene Blue, Nitrofurantoin, Pantoprazole sodium, Salicylic acid, Triclosan, Trihexyphenidyl hydrochloride, Trimetazidine dihydrochloride, Urethane, Xylitol, Aminoguanidine hydrochloride, Azelaic acid, Bithionol, Bronopol, Bucetin, Carsalam, Carzenide, Citiolone, Cloxiquine, Danthron, Dehydrocholic acid, Diethylcarbamazine citrate, Diiodohydroxyquinoline, DL-Panthenol, Fluphenazine dihydrochloride, Halothane, Hexylresorcinol, Piperazine, Sulfabenzamide, Terpin hydrate, Tyloxapol, Resorcinol, Hydroquinone, Triacetin, Butamben, Butylparaben, Succinylsulfathiazole, Docusate Sodium, Amodiaquine dihydrochloride dihydrate, Nitroxoline, Chlormadinone acetate, Cephalothin, Cefazolin Sodium, Cefixime, Lercanidipine hydrochloride, Benzyl benzoate, Benzyl alcohol, Clioquinol, Acetohydroxamic acid, Gallic acid, Levofloxacin hydrate, Folic acid, 2,2'-Dihydroxy-4-methoxybenzophenone, Diflunisal, Mebendazole, Dapson, Dextromethorphan hydrobromide hydrate, Fenoldopam mesylate, Itopride hydrochloride, Cefuroxime sodium, 5,5-Dimethyloxazolidine-2,4-dione, Alcaftadine, Ethosuximide, (+/−)-Sulfinpyrazone, Chlortrianisene, Diazoxide, Prochlorperazine dimaleate salt, Hexachlorophene, Isosorbide Mononitrate, Sodium sulfadiazine, Cyproheptadine hydrochloride, Teneligliptin hydrobromide, Prasugrel Hydrochloride, Desogestrel, Brexpiprazole, Lesinurad, Tedizolid Phosphate, Armodafinil, Ciclesonide, Cefmenoxime hydrochloride, Dantrolene sodium hemiheptahydrate, Atipamezole hydrochloride, Atipamezole, Etoricoxib, Sulisobenzone, Sulpiride, Parecoxib, Eslicarbazepine Acetate, Hydroquinidine, Glycopyrrolate, Tiagabine hydrochloride, Atazanavir, Fusidate Sodium, Molsidomine, Rebeprazole sodium, Sivelestat sodium tetrahydrate, Lidocaine hydrochloride, Procaine, Benzocaine hydrochloride, Etonogestrel, Hydroxyprogesterone caproate, Tiagabine, Gluconolactone, Povidone iodine, Terazosin HCl, Protirelin, Loxoprofen, Sildenafil Mesylate, Efavirenz, Vitamin E, Rivastigmine, Deoxycholic acid, Escin, Oxybenzone, Guanfacine Hydrochloride, D panthenol, CarbinoxaMine Maleate, Saxagliptin hydrate, b-AP15, Pimecrolimus, AZD2932, LCL161, RG-7112, XL388, Epoxomicin, LY2874455, LY2090314, Tepotinib (EMD 1214063), RN486, GDC-0032, Go6976, MLN2480, Marimastat (BB-2516), Motolimod (VTX-2337), Dyngo-4a, R05126766 (CH5126766), GKT137831, ABC294640, BAF312 (Siponimod), CID755673, Idasanutlin (RG-7388), PF-04418948, GSK2801, NVP-TNKS656, G007-LK, FLLL32, Vidofludimus, FRAX597, HPOB, JIB-04, PFI-2 HCl, ML324, AZ5104, MS436, Q-VD-Oph, Z-DEVD-FMK, PFI-3, HTH-01-015, K-Ras(G12C) inhibitor 12, ERK5-IN-1, AZD3965, URMC-099, Bay 11-7085, Poziotinib (HM781-36B), BRD7552, LY2119620, Pepstatin A, MG-101 (ALLN), Calpeptin, Anisomycin, Ascomycin (FK520), WS3, WS6, AP-III-a4 (ENOblock), E3330, XEN445, FTI 277 HCl, MG149, DMOG, Uprosertib (GSK2141795), TAM-1, DDR1-IN-1, UM729, GNF-5837, Afuresertib (GSK2110183), FR 180204, EW-7197, UMI-77, PF-06463922, SB273005, Decernotinib (VX-509), Vacquinol-1, G-749, Erythromycin Cyclocarbonate, Piperlongumine, GDC-0623, 4SC-202, CL-387785 (EKI-785), ODM-201, AT13148, LMK-235, UNC0379, A-366, GSK2830371, GSK-LSD1 2HCl, UNC2025, AGK2, Ledipasvir (GS5885), GSK J1, Anacardic Acid, LRRK2-IN-1, SB-334867, Reversine, BRD4770, Splitomicin, Abscisic Acid (Dormin), CAY10603, RBC8, BQU57, UM171, UNC0631, EI1, PX-478 2HCl, CPI-169, Tasquinimod, MI-2 (Menin-MLL Inhibitor), MI-3 (Menin-MLL Inhibitor), GSK1324726A (I-BET726), PI-3065, SD-208, Niraparib (MK-4827) tosylate, LDN-214117, TH287, TH588, Lomitapide Mesylate, Cerdulatinib (PRT062070, PRT2070), SU9516, DTP3, LDC1267, Remodelin, D 4476, PF-431396, Pilaralisib (XL147), Voxtalisib (XL765, SAR245409), MI-773 (SAR405838), Peficitinib (ASP015K, JNJ-54781532), SB225002, PND-1186 (VS-4718), Defactinib (VS-6063, PF-04554878), CB-839, CPI-360, Kartogenin, Obeticholic Acid, GSK2578215A, CH5183284 (Debio-1347), SU5402, Picropodophyllin (PPP), NPS-1034, Omaveloxolone (RTA-408), L-685,458, PF-4989216, LCZ696, YK-4-279, SP2509, OF-1, PIK-III, Salirasib, SecinH3, ML141, BG45, PS-1145, AZD6738, AZD8186, LY2409881, Liproxstatin-1, LY2584702 Tosylate, A-438079 HCl, Verdinexor (KPT-335), VX-11e, CH-223191, FIIN-2, BMH-21, CCG-1423, SBE 13 HCl, Monomethyl auristatin E (MMAE), Bikinin, BLZ945, BRD73954, NU1025, AZD3839, LFM-A13, PRT-060318 2HCl, SB239063, SCR7, ANA-12, Ro-3306, EPZ015666(GSK3235025), KNK437, VER155008, SCi, BPTES, 6-Thio-dG, TRx0237 (LMTX) mesylate, D-Luciferin, Dovitinib (TKI258) Lactate, Cabotegravir (GSK744, GSK1265744), AZ6102, STF-083010, Elacridar (GF120918), SU6656, Emricasan, Akti-1/2, Coelenterazine, Smoothened Agonist (SAG) HCl, Sunitinib, Dasatinib Monohydrate, Combretastatin A4, Erlotinib, Docetaxel Trihydrate, SRT2104 (GSK2245840), Purvalanol A, ORY-1001 (RG-6016) 2HCl, GSK2879552 2HCl, GNE-317, Pexmetinib (ARRY-614), GSK503, EPZ011989, AT7519 HCl, Afatinib (BIBW2992) Dimaleate, MHY1485, AMG319, AI-10-49, MI-136, Pexidartinib (PLX3397), 4-Hydroxytamoxifen, Licochalcone A, CB1954, SGC707, Cyclo (-RGDfK), I-BRD9, Endoxifen HCl, BI-847325, Cyclo (RGDyK), SirReal2, SGI-7079, AZD3264, Eliglustat Tartrate, Ulixertinib (BVD-523, VRT752271), Tenofovir Alafenamide (GS-7340), 8-Bromo-cAMP, Dibutyryl-cAMP (Bucladesine), SC79, Oltipraz, Oleuropein, LJH685, LJ1308, ONO-4059 analogue, BQ-123, AMI-1, SBI-0206965, CC-223, Spautin-1, Xanthohumol, Sodium Tauroursodeoxycholate (TUDC), GSK621, SW033291, PFI-4, Dp44mT, Epacadostat (INCB024360), PD-1/PD-L1 inhibitor 1, BMS202 (PD-1/PD-L1 inhibitor 2), MCB-613, Isoxazole 9 (ISX-9), BIO-acetoxime, Kenpaullone, Bromodeoxyuridine (BrdU), DEL-22379, Tiplaxtinin (PAI-039), Bay K 8644, WZB117, DASA-58, STF-31, VR23, KD025 (SLx-2119), GSK2292767, NCT-501, 0411, 0412, KC7F2, PX-12, Ozanimod (RPC1063), ETC-1002, EPI-001, TIC10, PLX7904, P7C3, AZD3759, L755507, Favipiravir (T-705), SBC-115076, Napabucasin, FG-2216, VPS34-IN1, SKF38393 HCl, Ripasudil (K-115) hydrochloride dihydrate, Entrectinib (RXDX-101), SKF96365, U73122, Otenabant (CP-945598) HCl, PF-03084014 (PF-3084014), Cobimetinib (GDC-0973, RG7420), ASP3026, Vorapaxar, GlyH-101, Tubercidin, Mirin, C-DIM12, K03861, CB-5083, Z-VAD-FMK (Caspase Inhibitor VI), Sotagliflozin (LX4211), SCH58261, ZM241385, NSC59984, GSK1016790A, GSK591, MS023, ICI-118551 Hydrochloride, Acalabrutinib (ACP-196), GMX1778 (CHS828), BMS-582949, BAY 41-2272, Resiquimod, Radotinib, Riociguat (BAY 63-2521), Sivelestat (ONO-5046), Molidustat (BAY 85-3934), GNF-7, Halofuginone, Mitomycin C, PD0166285, NSC348884, RSL3, ON123300, Cucurbitacin B, AMG 337, GSK481, Daprodustat (GSK1278863), Ro 61-8048, Wnt agonist 1, BI-7273, PF-CBP1 HCl, SBI-0640756, Pimavanserin, FPS-ZM1, Oclacitinib, ML264, LTX-315, BI-78D3, PF-06447475, Enasidenib (AG-221), Ivosidenib(AG-120), HLCL-61 HCL, PF-8380, Bitopertin, AS1842856, RS-1, MK-886 (L-663,536), IC261, SB366791, SMER28, Ponesimod, IQ-1, PRI-724, FCCP, IMR-1, CCF642, Fatostatin HBr, NQDI-1, Selonsertib (GS-4997), Olmutinib (HM61713, BI 1482694), SR-12813, Kobe0065, 5-Iodotubercidin, 7,8-Dihydroxyflavone, MLR-1023, LY3023414, ITSA-1 (ITSA1), Bivalirudin Trifluoroacetate, Eptifibatide Acetate, Lypressin Acetate, Octreotide Acetate, Atosiban Acetate, Oxytocin (Syntocinon), Salmon Calcitonin Acetate, GHRP-2, Nafarelin Acetate, Perifosine (KRX-0401), Pemetrexed, Gemcitabine HCl, Carboplatin, Leucovorin Calcium Pentahydrate, Pamidronate Disodium, Gabapentin HCl, Galanthamine HBr, Granisetron HCl, Heparin sodium, Biapenem, Daptomycin, Dorzolamide HCl, Mizoribine, Polymyxin B sulphate, Teicoplanin, Varenicline Tartrate, Perindopril Erbumine, Ibuprofen Lysine, Palbociclib (PD0332991) Isethionate, Cytarabine, L-Glutamine, Gadodiamide Hydrate, Nedaplatin, Penicillamine, Etidronate, Tranexamic Acid, D-glutamine, Disodium Cromoglycate, (−)-Tetramisole, Metformin HCl, Ticlopidine HCl, ATP, Procarbazine HCl, D-Cycloserine, Sodium butyrate, Sodium orthovanadate, Taurine, Clindamycin Phosphate, Lisinopril, Fosinopril Sodium, Fudosteine, Gabapentin, Kanamycin sulfate, Donepezil HCl, Neostigmine Bromide, Salbutamol Sulfate, Tobramycin, NAD+, Lomefloxacin HCl, Hydralazine HCl, Oxacillin sodium monohydrate, Neomycin sulfate, Streptomycin sulfate, Vancomycin HCl, Calcium Levofolinate, L-NAME HCl, Hygromycin B, Plerixafor 8HCl (AMD3100 8HCl), Geneticin (G418 Sulfate), Palonosetron HCl, Miltefosine, Danofloxacin Mesylate, Amikacin disulfate, (R)-baclofen, Creatinine, Amikacin hydrate, Ibandronate sodium, Abacavir sulfate, L-Arginine HCl (L-Arg), Thiamine HCl (Vitamin B1), Pemirolast potassium, Sodium Monofluorophosphate, Dexamethasone Sodium Phosphate, Colistin Sulfate, Gentamicin Sulfate, Netilmicin Sulfate, Hexamethonium Bromide, Bismuth Subcitrate Potassium, Tetramisole HCl, Clodronate Disodium, Histamine Phosphate, Succinylcholine Chloride Dihydrate, Terbutaline Sulfate, Mildronate, Eprazinone 2HCl, Chloroquine Phosphate, Ceftriaxone Sodium Trihydrate, Sodium Gluconate, Nefopam HCl, Paromomycin Sulfate, Ribostamycin Sulfate, Minocycline HCl, Capreomycin Sulfate, Proflavine Hemisulfate, Apramycin Sulfate, Isepamicin Sulphate, Amifostine, Calcium Gluceptate, Ceftazidime Pentahydrate, Tolmetin Sodium, Hydroxychloroquine Sulfate, Dihydrostreptomycin sulfate, Sisomicin sulfate, Antimonyl potassium tartrate trihydrate, Eprodisate disodium, Pralidoxime chloride, Eflornithine hydrochloride hydrate, Glutathione, L-Ornithine, Cefradine, Sildenafil, Fosbretabulin (Combretastatin A4 Phosphate (CA4P)) Disodium, Dorsomorphin 2HCl, Aprotinin, Blasticidin S HCl, LDN-193189 HCl, LB-100, XL413 (BMS-863233), Rilmenidine Phosphate, Pemetrexed Disodium Hydrate, MCC950(CP-456773), Disodium (R)-2-Hydroxyglutarate, BEC HCl, RGD (Arg-Gly-Asp) Peptides, APT-STAT3-9R): Selleck.

2) Crypt culture solution: Intestinal Epithelial Organoid CuLture with IntestiCult™ Organoid Growth Medium (Mouse): STEMCELL Technologies Inc.

3) Matrigel: Matrigel® GFR and Phenol Red-Free Basement Membrane Matrix: Corning
4) Antibiotics solution (penicillin/streptomycin): Gibco 1.1.3 Main Instrument 1) X-ray biological irradiator (X-RAD320ix): PXi
2) Synergy 2 multi-mode microplate reader: BioTek Instruments, Inc.

1.1.4 Master Solution

Digestive solution: 2.978 g $C_{10}H_{14}N_2Na_2O_8 \cdot 2H_2O$ were weighed and 1 L HBSS was added to regulate a pH=8.

1.2 Experimental Methods 1.2.1 In Vitro Medicament Screening Experiment on Crypt Stem Cells $Lgr5^+$ of Mice 1) Lgr5-GFP mice were sacrificed by cervical dislocation, and enterocoelia was opened and the whole small intestine was taken out, and then the small intestine was put to a pre-cooled HBSS buffer solution to remove mesentery and adipose tissues as much as possible, and dissected longitudinally to wash out contents of the small intestine.

2) Villi and contents inside the intestinal cavity were scraped by a glass slide, and then the remaining intestinal cavity was washed for once to twice.

3) The whole small intestine was quickly cut into 5 mm intestinal segments.

4) The intestinal segments were transferred to a 50 mL centrifugal tube, and 25 mL HBSS and 250 µL penicillin/streptomycin solution were added for incubation for 10 min at room temperature, and then the centrifugal tube was slightly inverted to mix evenly for 2-3 times.

5) Supernatant was absorbed, and 10 mL new HBSS was added to wash the intestinal segments for 2-3 times till the final intestinal segments were cleaned thoroughly, then a 70 µm filter sieve was used for filtering to retain the remaining intestinal segments.

6) The intestinal segments were transferred to a 50 mL centrifugal tube, and added to a 10 mL pre-blended digestive solution for incubation for 5 min at room temperature.

7) The centrifugal tube was shaken violently or swirled for several seconds, and then a 70 µm filter sieve was used for filtering.

8) The intestinal segments were transferred to a new 50 mL centrifugal tube, and a 10 mL digestive solution was added for incubation on ice for 30 min, and then the centrifugal tube was shaken violently or swirled for several seconds, and then a 70 µm filter sieve was used for filtering. A black 96-well plate was put on an incubator for preheating during the incubation on ice.

9) The intestinal segments were transferred to a new 50 mL centrifugal tube, and 10 mL HBSS was added, then the centrifugal tube was shaken violently or swirled for several seconds, and a 70 µm filter sieve was used for filtering to retain filtrate.

10) 300 g filtrate was centrifuged for 10 min at 4° C.

11) Supernatant was removed, and crypt cells were precipitated and resuspended by a crypt cell culture solution, and then cell counting was performed microscopically.

12) Cells were diluted by a ratio of the crypt cell culture solution to matrigel=1:1 (v/v), so as to ensure that per 10 µL of mixed liquor contained about 100 crypt cells.

13) The preheated black 96-well plate was taken out, and 10 µL mixed liquor was added to the center of each well, and then the well plate was put to an incubator for 10 min at 37° C.

14) After the matrigel was solidified, each medicament in Bioactive Compound Library (790 types) was diluted by a medium to a final concentration of 10 µM, and then 100 µL was added to per well.

In certain embodiments, the concentration of Rivastigmine in a composition administered to a subject can be about 1 µM to about 100 µM, about 5 µM to about 50 µM, or about 10 µM. In certain embodiments, the concentration of Rivastigmine administered to a subject can be about 0.1 mg/kg to about 10 mg/kg, about 1 mg/kg to about 5 mg/kg, or about 2 mg/kg to about 3 mg/kg, in which the dosage of the Rivastigmine (mg) is based on the weight of the subject (kg).

15) The 96-well plate was put on a multi-mode microplate reader to read fluorescence intensity under the conditions of excitation wavelength at 485 nm and emission wavelength at 528 nm, and to record the values on the same day.

16) Crypt cells were irradiated with 10 Gy radiation, and the fluorescence intensity for consecutive 10 d after irradiation was recorded; afterwards, the background fluorescence intensity of a blank control was removed, and a fluorescence intensity curve was drawn; and the test results were shown in FIGS. 1-4.

1.2.2 Experiment for Verifying the Survival Rate of Mice at a Lethal Dose

Mice were subjected to 10 Gy whole body irradiation with an X-ray biological irradiator in Department of Medicine having a dose rate of 1.5 Gy/min; and before irradiation, mice were intraperitoneally injected the medicament screened out via an in vitro experiment, and then continuously raised in a temporary storage room of the animal center after irradiation. A survival curve was recorded and the results were shown in FIGS. 5-12.

1.3 Experimental Result 1.3.1 Results of the In Vitro Medicament Screening Experiment on Crypt Stem Cells $Lgr5^+$ of Mice Ionizing radiation induces the death of intestinal stem cells; $Lgr5^+$ epithelial cells were proved to be associated with the repair of radiation damage; further, $Lgr5^+$ epithelial cells can develop into an organoid structure under a 3D cultivation system in vitro; and such kind of organoid structure has a structure similar to in vivo crypt and thus, can simulate the in vivo conditions well.

Crypt stem cells $Lgr5^+$ separated from Lgr5-GFP mice in vivo carried GFP fluorescence, and the change of the mean fluorescence intensity (MFI) represented the proliferation of crypt stem cells Lgr5*.

In this experiment, 790 types of clinical medicaments were diluted to a final concentration of 10 µM, and then added to a medium containing separated crypt stem cells $Lgr5^+$ one by one; then 10 Gy irradiation was provided to record the initial GFP fluorescence intensity and the GFP fluorescence intensity 10 d after irradiation, and then a luminescence curve was drawn after minus the background value, thus showing the influences of the medicaments on the proliferation of $Lgr5^+$ stem cells after irradiation. For the proliferation of the crypt stem cells $Lgr5^+$ of the mice without irradiation in all control groups as shown in FIGS. 1-4, the separated crypt stem cells $Lgr5^+$ had sprouting proliferation as time flies to form spheroids; and meanwhile, the fluorescence intensity would increase. All IR groups in FIGS. 1-4 showed the proliferation of $Lgr5^+$ stem cells of mice irradiated with 10 Gy radiation. In view of individual differences of different mice, there were corresponding control groups for each group.

Figure 2:
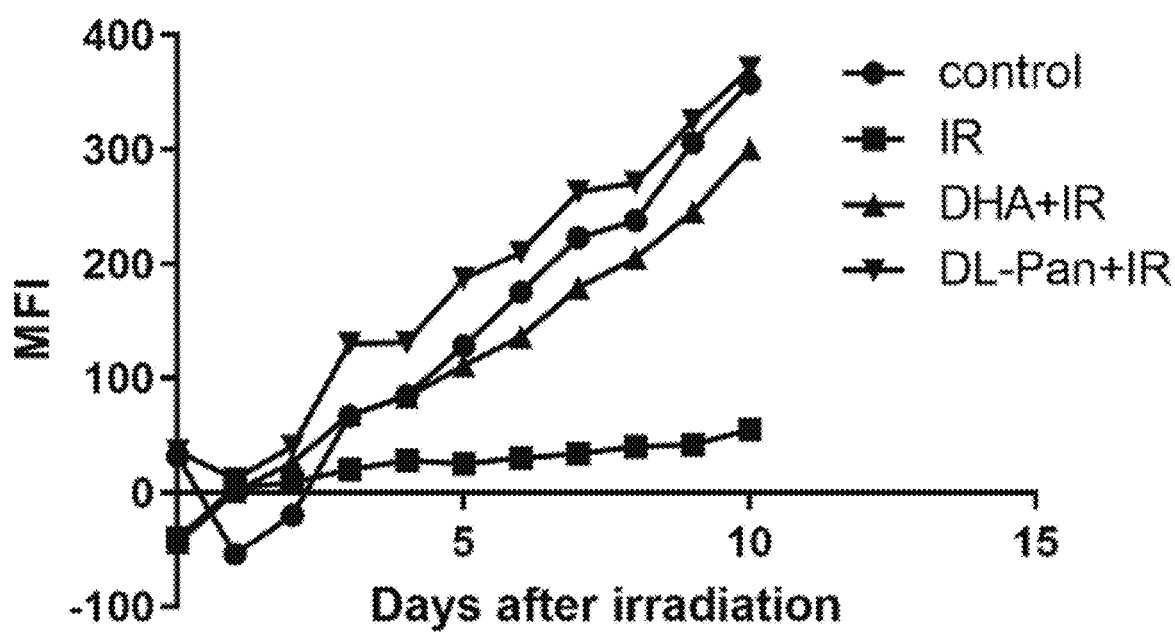
Figure 3:
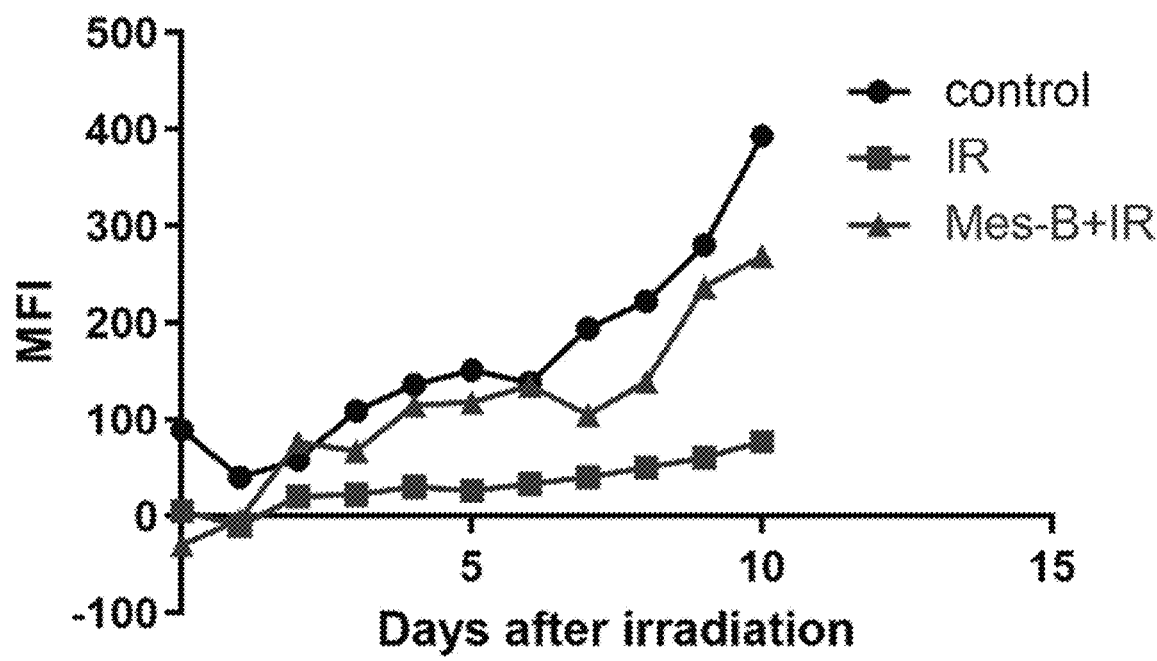
Figure 4:
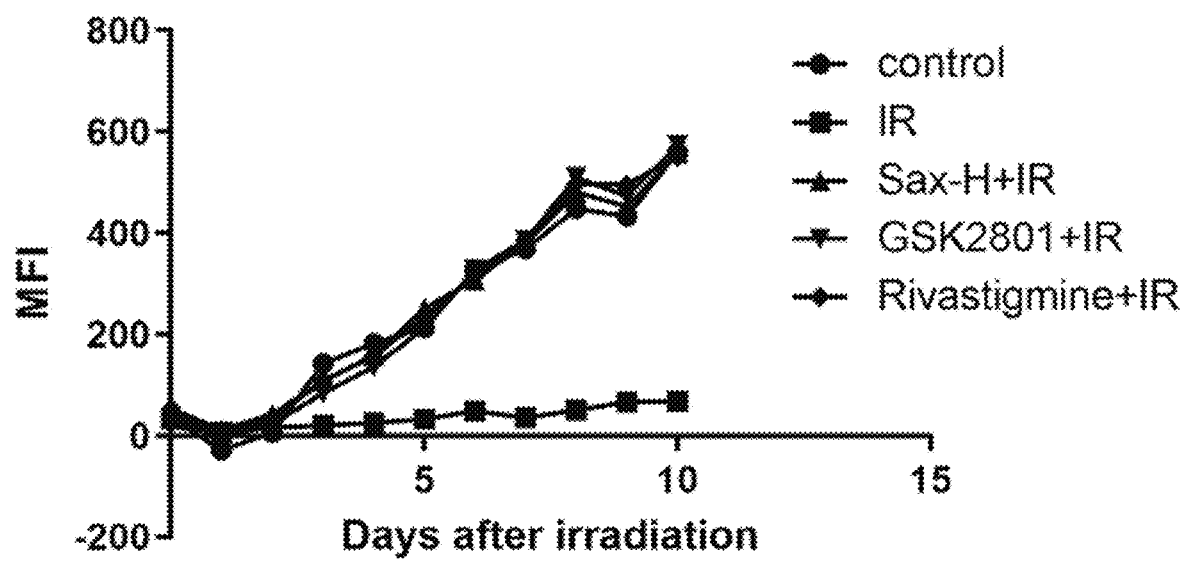

As shown in FIG. 1, Donepezil HCl (Don-H) and Pralidoxime chloride (Pra-C) were administered in vitro to promote the proliferation of $Lgr5^+$ stem cells after irradiation; and the increment of the $Lgr5^+$ stem cells improved 6.2 and 4.8 times compared with IR groups, respectively. As shown in FIG. 2, Dehydrocholic acid (DHA) and DL-Panthenol (DL-Pan) were administered to promote the proliferation of Lgr5⁺ stem cells after irradiation; and the increment of the Lgr5⁺ stem cells improved 3.4 and 3.5 times compared with IR groups, respectively. As shown in FIGS. 3-4, Mesoridazine Besylate (Mes-B), GSK2801, Saxagliptin hydrate (Sax-H), and Rivastigmine also can promote the proliferation of Lgr5⁺ stem cells after irradiation; and the increment of the Lgr5⁺ stem cells improved 4.2, 14.7, 15.9 and 14.2 times compared with IR groups, respectively.

1.3.2 Survival Rate Result of Mice after Administering Medicaments at a Lethal Dose After the experiment of 1.3.1, 8 medicaments having better efficacy were selected for animal experimental verification, including Don-H, Pra-C, DHA, DL-Pan, Mes-B, Sax-H and Rivastigmine, respectively.

4 to 6 week-age C57BL/6 mice were selected as experimental subjects, and divided into control groups and experimental groups, and subjected to 10 Gy whole body irradiation with a dose rate of 1.5 Gy/min; mice in the experimental subjects were respectively intraperitoneally injected the medicaments screened half an hour before irradiation, and the survival time was recorded after irradiation. Among the medicaments, water-soluble Don-H, Pra-C and DL-Pan are dissolved by normal saline, and others were dissolved by 5 g/100 mL DMSO+edible oil. The medicament was prepared into a stock solution having a corresponding concentration according to the volume that 20 g mice were intraperitoneally injected 100 μL medicament.

Figure 5:
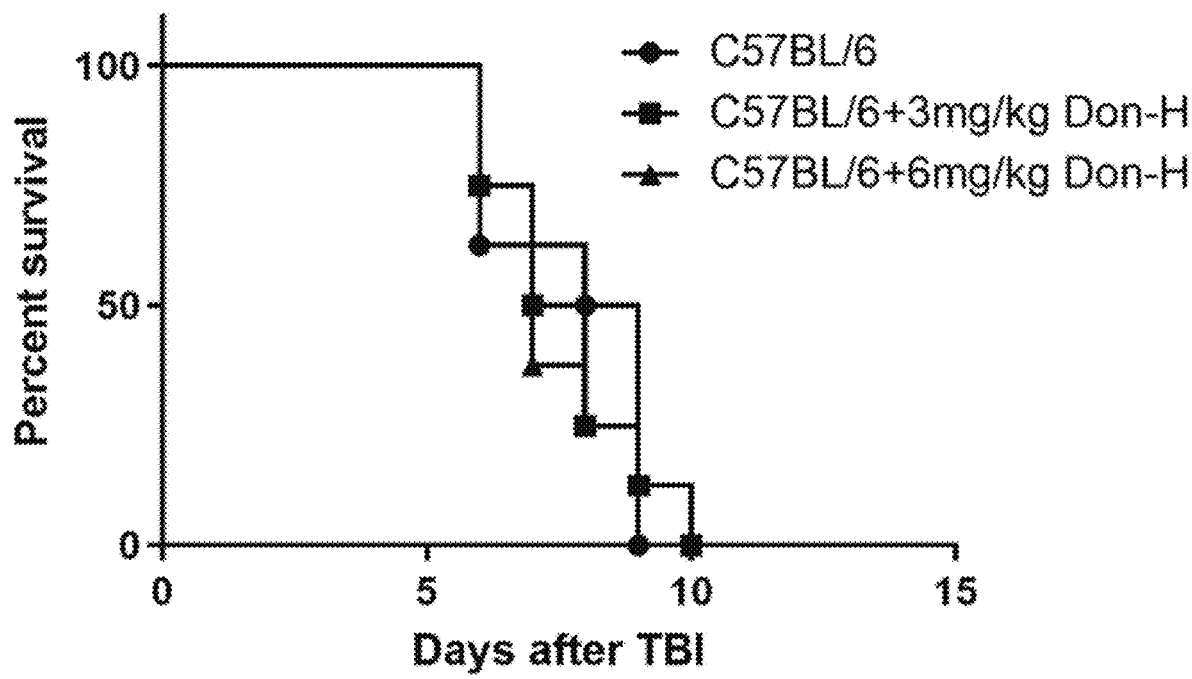
FIGS. 5-12 show survival time of mice in different groups.
Figure 6:
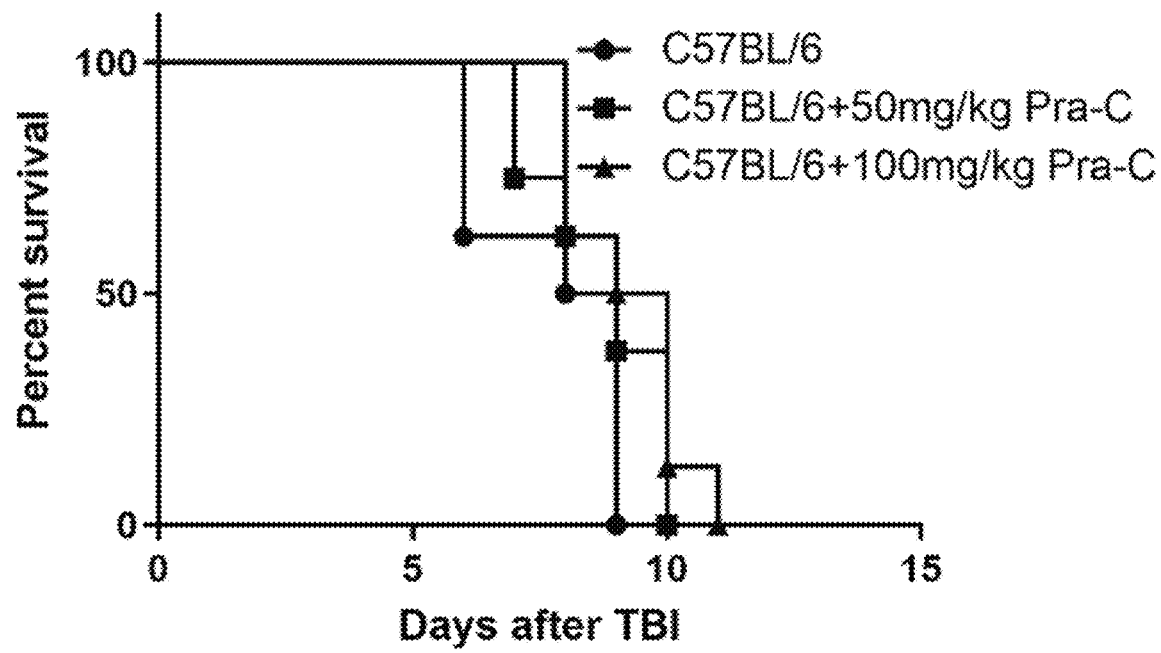
Figure 7:
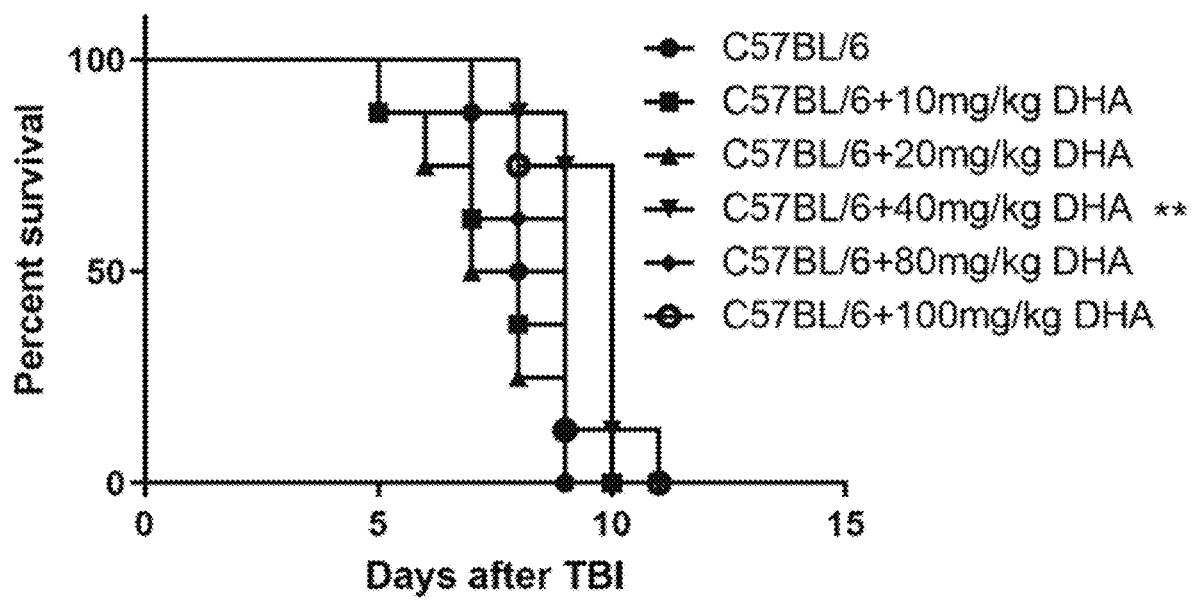
Figure 8:
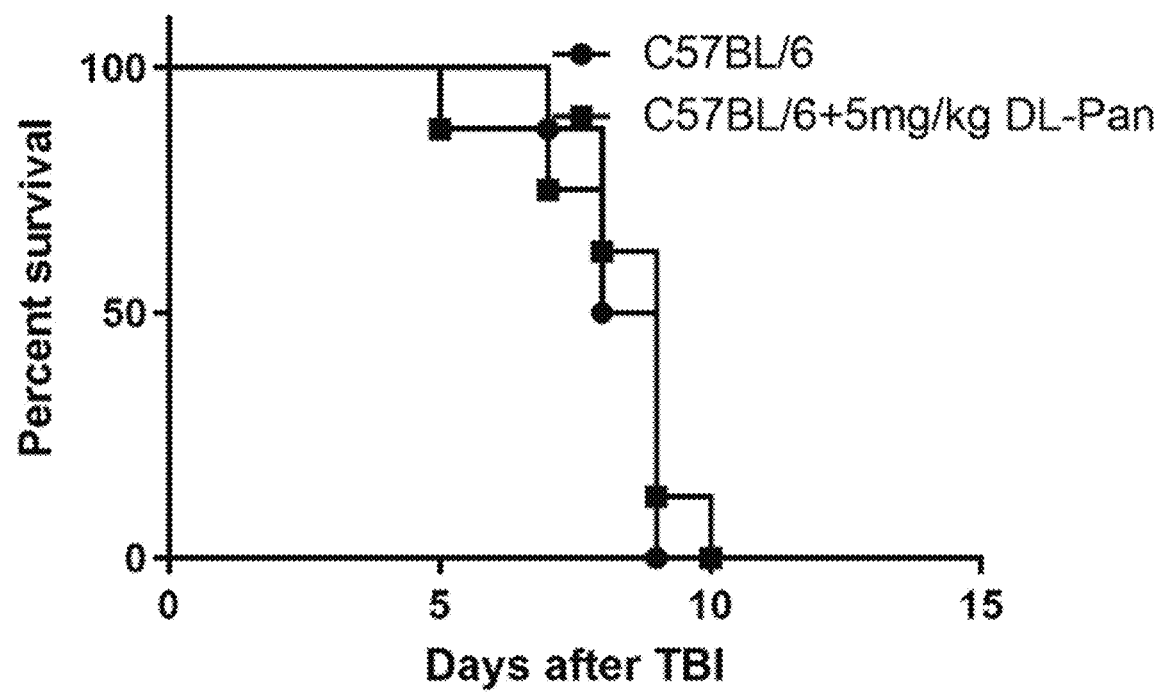
Figure 9:
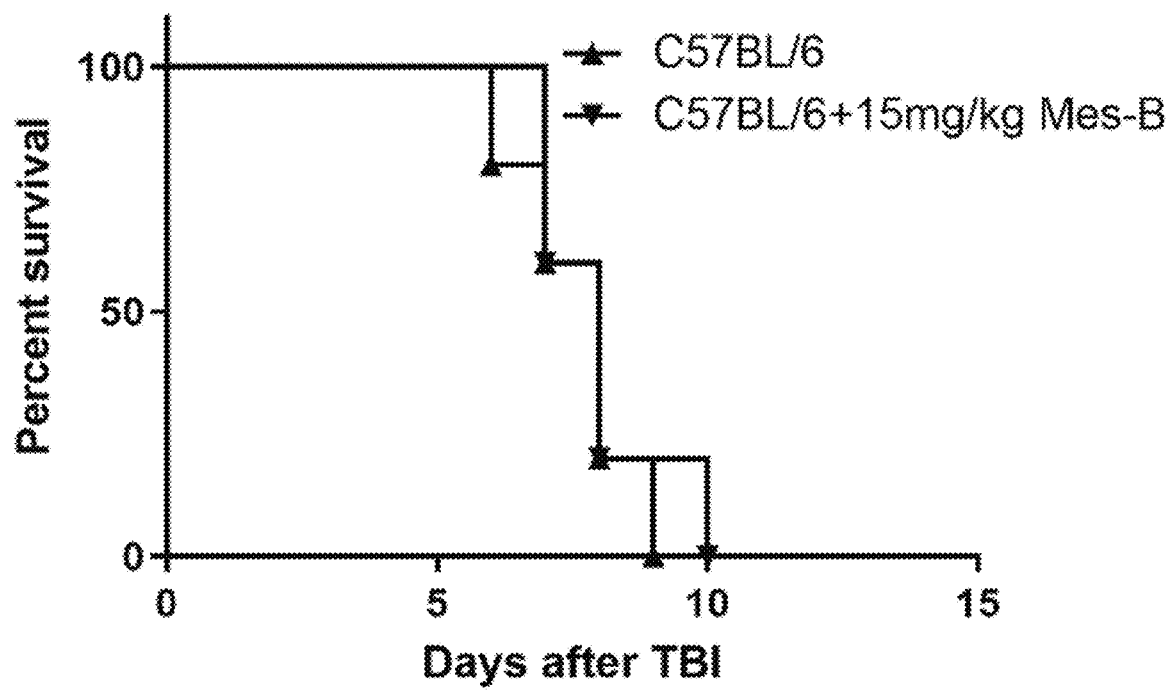
Figure 10:
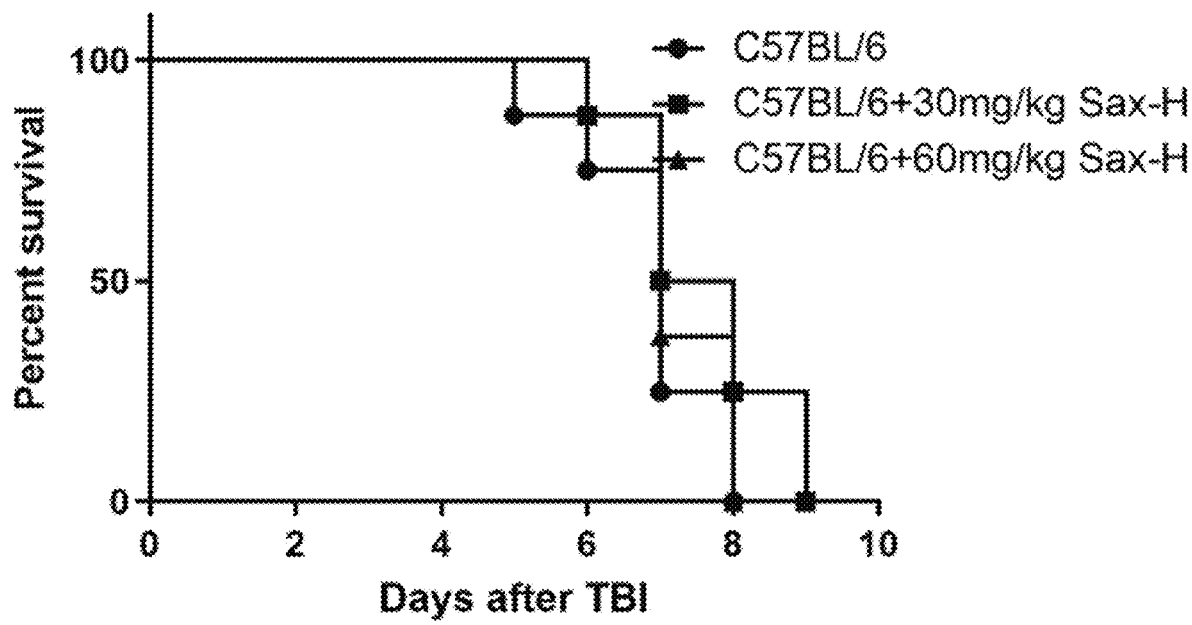
Figure 11:
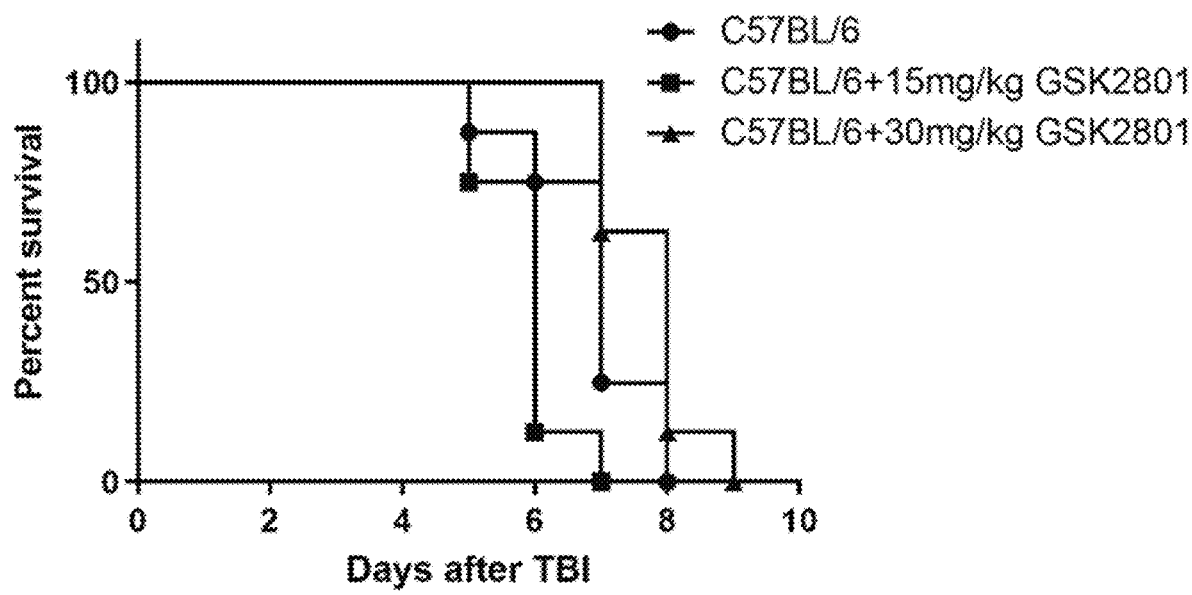
Figure 12:
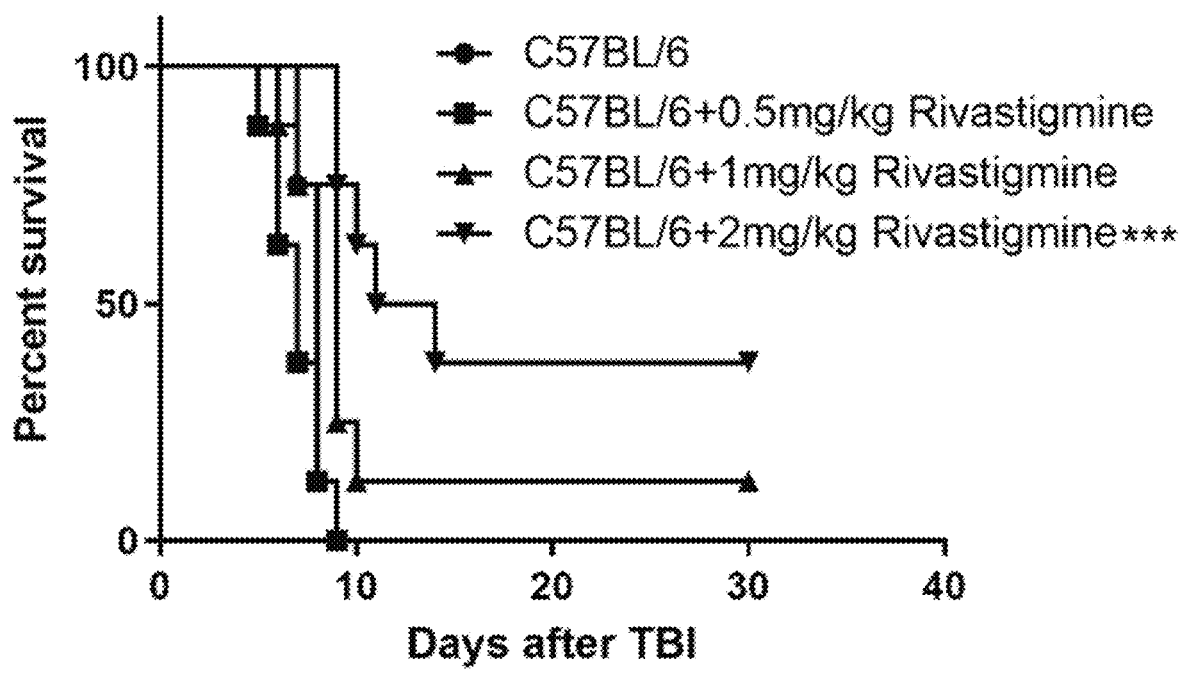

As shown in FIGS. 5-12, all the mice in control groups died within 10 d after receiving 10 Gy whole body irradiation. As shown in FIG. 5, the administration of 3 mg/kg and 6 mg/kg Don-H did not improve the survival time of the mice. As shown in FIG. 6, the administration of 50 mg/kg and 100 mg/kg Pra-C did not improve the survival time of the mice, either. As shown in FIG. 7, the administration of 10 mg/kg, 20 mg/kg, 60 mg/kg, 80 mg/kg, and 100 mg/kg DHA did not improve the survival time of the mice, while 40 mg/kg DHA may extend the death time of the mice for 2 d, and there was statistical significance ( represents $P<0.01$). FIGS. 8-11 respectively represent influences of four medicaments DL-Pan, Mes-B, Sax-H and GSK2801 on the survival time of mice after receiving irradiation, and there was no statistical significance. FIG. 12 shows an influence of Rivastigmine on the survival time of mice after receiving irradiation; there were still survival mice after 30 d for the groups which were subjected to irradiation after being treated by 1 mg/kg and 2 mg/kg Rivastigmine; for the 2 mg/kg Rivastigmine group, the survival rate was greater than 40%; and there was statistically significant (* represents $P<0.001$) compared with the control group.

It is apparent that the above examples are merely listed for clear description, and are not intended to limit the embodiments. Those of ordinary skill in the art may make modifications or variations in other forms based on the above description. There is no need and no way to exhaust all of the embodiments. Obvious changes or variations made thereto shall still fall within the protection scope of the disclosure.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

As used herein, the term "subject" refers to an animal, needing or desiring delivery of the benefits provided by Rivastigmine or compositions thereof. The animal may be for example, humans, pigs, horses, goats, cats, mice, rats, dogs, apes, fish, chimpanzees, orangutans, guinea pigs, hamsters, cows, sheep, birds, chickens, as well as any other vertebrate or invertebrate. These benefits can include, but are not limited to, the treatment of a health condition, disease or disorder; prevention of a health condition, disease or disorder; immune health; enhancement of the function of an organ, tissue, or system in the body. The preferred subject in the context of this invention is a human, mouse, rat, or rhesus monkey. The subject can be of any age or stage of development, including infant, toddler, adolescent, teenager, adult, or senior.

As used herein, the terms "therapeutically-effective amount," "therapeutically-effective dose," "effective amount," and "effective dose" are used to refer to an amount or dose of a compound or composition that, when administered to a subject, is capable of treating, preventing, or improving a condition, disease, or disorder in a subject or that is capable of providing enhancement in health or function to the immune system or an organ, tissue, or body system. In other words, when administered to a subject, the amount is "therapeutically effective." The actual amount will vary depending on a number of factors including, but not limited to, the particular condition, disease, or disorder being treated, prevented, or improved; the severity of the condition; the particular organ, tissue, or body system of which enhancement in health or function is desired; the weight, height, age, and health of the patient; and the route of administration.

By "reduces" is meant a negative alteration of at least 1%, 5%, 10%, 25%, 50%, 75%, or 100%.

By "increases" is meant as a positive alteration of at least 1%, 5%, 10%, 25%, 50%, 75%, or 100%.

What is claimed is:

1. A method of treating radiation sickness, the method comprising administering an effective amount of a composition comprising Rivastigmine to a human in need of treatment for radiation sickness.

2. The method according to claim 1, wherein the radiation is ionizing radiation.

3. The method according to claim 2, wherein the ionizing radiation comprises radiation from a ray and a radioactive substance.

4. The method according to claim 3, wherein the ray is an X-ray, $\alpha$-ray, $\beta$-ray, $\gamma$-ray, neutron ray, negative $\pi$-meson ray or heavy ion beam.

5. The method according to claim 4, wherein the heavy ion beam is a helium ion beam, carbon ion beam, nitrogen ion beam, oxygen ion beam, or neon ion beam.

6. The method according to claim 1, wherein the composition further comprises a medicament carrier and/or a pharmaceutical adjuvant.

7. The method according to claim 6, wherein the medicament carrier is a microcapsule, a microsphere, a nanoparticle, or lipidosome.

8. The method according to claim 6, wherein the pharmaceutical adjuvant is a solvent, a propellant, a solubilizer, a cosolvent, an emulsifier, a colorant, a binding agent, a disintegrant, a filler, a lubricant, a wetting agent, an osmotic pressure regulator, a stabilizer, a flow aid, a corrigent, a preservative, a suspending agent, a coating material, an aromatic, an anti-binding agent, a chelating agent, a penetration enhancer, a pH regulator, a buffering agent, a plasticizer, a surfactant, a foaming agent, an antifoaming agent, a thickener, a clathrate compound, a humectant, an absorbent, a diluent, a flocculant, a deflocculant, a filter aid, or a release retardant.

9. The method according to claim 1, wherein the composition is a powder, a tablet, a granule, a capsule, a solution, an emulsion, a suspension, or an injection.

* * * * *